United States Patent
Lee et al.

(10) Patent No.: US 6,187,556 B1
(45) Date of Patent: Feb. 13, 2001

(54) **COMPOSITION, KIT, AND METHOD FOR DETECTING *HELICOBACTER PYLORI* IN BIOPSY**

(76) Inventors: Jong-Hwa Lee, Yukyoung Apt. 105-109, Yobang-ri, Seonggeo-eup, Cheonan-city, Choongcheongnam-do; Hak-Sung Lee, Deokpoong 1-dong 420-52, Hanam-city Kyungki-do; Im-Hwan Roe, Doosan Apt. 324-1401, Areum-maeul, Maesong dong, Bundang-ku, Seongnam-city, Kyungki-do; Jung-Taik Kim, Hanyang Apt. 314-1601, Seohyeon-dong 91, Bundang-ku, Seongnam-city, Kyungki-do; Yung-Chil Hah, Hanyang Apt. 51-1201, Apgoojeong-dong, Kangnam-ku, Seoul; Tae-Boo Choe, Walkerhill Apt. 52-501, Kwangjang-dong 145-8, Kwangjin-ku, Seoul, all of (KR)

( * ) Notice: Under 35 U.S.C. 154(b), the term of this patent shall be extended for 0 days.

(21) Appl. No.: 09/445,072

(22) PCT Filed: Apr. 2, 1999

(86) PCT No.: PCT/KR99/00161

§ 371 Date: Dec. 2, 1999

§ 102(e) Date: Dec. 2, 1999

(87) PCT Pub. No.: WO99/51769

PCT Pub. Date: Oct. 14, 1999

(30) Foreign Application Priority Data

Apr. 3, 1998 (KR) .................................................. 98-11909

(51) Int. Cl.[7] .............................. C12Q 1/04; C12Q 1/58; G01N 33/53
(52) U.S. Cl. ................. 435/34; 435/12; 435/975
(58) Field of Search ................. 435/34, 12, 975

(56) References Cited

U.S. PATENT DOCUMENTS

| | | | |
|---|---|---|---|
| 5,420,016 | 5/1995 | Boguslaski et al. | 435/12 |
| 5,439,801 | 8/1995 | Jackson | 435/12 |

FOREIGN PATENT DOCUMENTS

| | | |
|---|---|---|
| 0 204 438 | 12/1986 | (EP) . |
| WO 97/30351 | 8/1997 | (WO) . |
| 9951769 A1 | * 10/1999 | (WO) . |

\* cited by examiner

*Primary Examiner*—Louise N. Leary
(74) *Attorney, Agent, or Firm*—Fish & Richardson, P.C.

(57) ABSTRACT

Disclosed are a composition for detecting *Helicobacter pylori* including urea 0.5 to 4 percent by volume, potassium phosphate 0.05 to 0.2 percent by volume, phenate reagent solution 0.8 to 1.7 percent by volume, an indicator having a $pK_a$ of 6.5 to 8.5, 0.002 to 0.005 percent by volume, and a balance of water, a kit for detecting *Helicobacter pylori* using the composition and detecting method using the composition can determine quickly and accurately whether or not an infection by *Helicobacter pylori* exists, can obtain the same determination results after an elapse of time and can be used easily in an endoscope chamber.

8 Claims, 2 Drawing Sheets

COMPOSITION, KIT, AND METHOD FOR DETECTING *HELICOBACTER PYLORI* IN BIOPSY

BACKGROUND OF THE INVENTION (a) Field of the Invention

This invention relates to detection of *Helicobacter pylori* (hereinafter called H. pylori), source bacterium of gastrointestinal disorders, and in particular relates to an H. pylori detecting composition produced by applying a phenate method for ammonium ion's quantitative determination to a conventional urease enzyme test and relates to a detecting kit and method using this composition.

(b) Description of the Related Art

H. pylori is noted as a source bacterium causing gastrointestinal disorders including gastric cancer and gastroduodenal ulcers, and the WHO has prescribed H. pylori as a typed carcinogen. Precise diagnosis, i.e., accurate detection of H. pylori, should be promoted to cure gastrointestinal disorders caused by this H. pylori. H. pylori detecting methods being used up to now can be divided mainly into two types, i.e., non-invasive tests not using an endoscope and invasive tests using an endoscope to get biopsy tissue for detection purposes.

Non-invasive tests include serology tests and $^{13}$C or $^{14}$C Breath tests. Serology tests measuring H. pylori antibodies have a problem in that the existence of the antibody does not necessarily mean that diseases are developing because it takes more than 6 months for antibody levels to drop after the cure of diseases. The $^{13}$C or $^{14}$C Breath test uses the principle that if urea marked with $^{13}$C or $^{14}$C is ingested, it is transformed into marked $CO_2$ in the stomach if H. pylori exists and detected in exhaled air. However, the method is not usually used because it involves high cost equipment.

On the other hand, invasive tests are more commonly used to detect H. pylori. Invasive tests detecting methods using biopsy tissues samples collected during an endoscoping includes histology, the PCR (Polymerase Chain Reaction) method, culturing, and the urease enzyme test. Histology is a method confirming the existence of H. pylori through general tissue research, the PCR method is a method confirming the existence of H. pylori by using chain reaction of polymerization enzyme, and culturing is a method of directly cultivating H. pylori from biopsy tissue. However, there is a problem in that all these methods are difficult and take much time, so they can not be used commercially.

The urease enzyme test, which can be used easily in the endoscope chamber and is the most efficient method, uses the fact that H. pylori produces urease enzyme which has a much higher degree of activity compared to other microorganisms. That is, if urease exists urea added in the detecting kit decomposes and ammonia is produced to cause pH to be increased making a pH indicator react and change color. A H. pylori detecting method measures the activity degree of urease like this. Commercialized kits using the urease enzyme test now are "CLOtest" (U.S. Pat. No. 4,748,113), "Hpfast" (U.S. Pat. No. 5,439,801) and "Pyloritek" (U.S. Pat. Nos. 5,314,804 and 5,420,016). Compositions used in "CLOtest" include 10~40 g/l of urea, 1~5 g/l of bactericide, an available quantity of $pK_a$ 6.5~8.5 indicator (phenol red) and the remainder being water, having a 5.0~6.5 pH. However, the CLOtest has problems in that the positive rate vary with the readers because the reaction speed of urease that the above compositions and H. pylori produce is slow. Therefore, diagnosis is possible only after about 24 hours and it is not possible to obtain diagnostic results on the endoscope examination date which requires that the patient inconveniently visit the hospital once more. Furthermore, the various colors appearing after more than 24 hours makes accurate diagnosis difficult. Hpfast is fundamentally similar to the CLOtest, but different in that cell wall detergent is added and uses as an indicator mixture of phenol red, methyl red, and bromothymol blue. With Hpfast, an H. pylori positive is determined from a dark green color of pH 6.2 and a light green color of pH 6.0 is determined as an H. pylori negative. However, the accurate reading of this dark green and light green colors is difficult. Pyloritek uses a multilayer test device differently from the above mentioned CLOtest and Hpfast, the main characteristics of this is that the urease reacting part and reacted product as an ammonia detecting part are on different layers and the pHs of each layers are different. Although Pyloritek can produce diagnosis results within one hour, the false positive rate increases if the determination time exceeds one hour. Therefore, there is an increasing possibility of false positives if an accurate reaction time is not adhered to during the endoscope examination.

Moreover, the above mentioned urease enzyme methods including the CLOtest, Pyloritek, etc. could also react with the small amounts of low activity urease which bacilli such as Staphylococcus hominis, Streptococcus salivarius, E. aerofaciens, L. fermentum, etc. have and false positive rates could be increased in cases of long decision times.

SUMMARY OF THE INVENTION

The present invention is designed to solve the above mentioned problems of the conventional technology by providing a H. pylori detecting composition, a H. pylori kit, and a method for using the above composition which allows the rapid and accurate determination of whether or not a H. pylori infection exists, which is the source bacterium that causes gastrointestinal disorders. The present invention also provides the same test results after a period of time passed, and it can easily be used in the chamber of an endoscope.

In order to achieve the above described purpose of this invention, this invention first provides H. pylori detecting composition including urea from 0.5 to 4 vol %, $KH_2PO_4$ from 0.05 to 0.2 vol %, phenate reagent solution from 0.8 to 1.7 vol %, an indicator from 0.002 to 0.005 vol % having a pKa of from 6.5 to 8.5 and a balance of water. Among the above described constituents, said phenate reagent solution from 0.8 to 1.7 vol % is preferably composed of manganous sulfate solution from 0.5 to 1 vol %, hypochlorite reagent from 0.2 to 0.5 vol % and phenate reagent from 0.1 to 0.2 vol % and the above described indicator is preferably phenol red. Moreover, said composition more preferably comprises gelling agent from 0.5 to 2 vol %. Especially said composition most preferably comprise 2 vol % urea, 0.05 vol % $KH_2PO_4$, 1 vol % manganous sulfate solution, 0.5 vol % hypochlorite reagent, 0.2 vol % phenate reagent, 0.0025 vol % phenol red, 1 vol % agar and a balance of water. And said composition preferably has pH from 6.0 to 7.8.

Second, this invention is made from the above described composition and provides an H. pylori detecting kit including biopsy tissue receptical test device, positive control produced by further adding 10~20 μl of 0.1 N NaOH solution to said constituents and negative control made of said constituents wherein no biopsy tissue is placed.

Third, this invention provides an H. pylori detecting method from biopsy tissue including stages of reacting biopsy tissue with said composition and observing color change of said composition.

BRIEF DESCRIPTION OF THE DRAWINGS

The accompanying drawings, which are incorporated in and constitute a part of the specification, illustrate an embodiment of the invention, and, together with the description, serve to explain the principles of the invention.

DETAILED DESCRIPTION OF THE PREFERRED EMBODIMENTS

Figure 1:
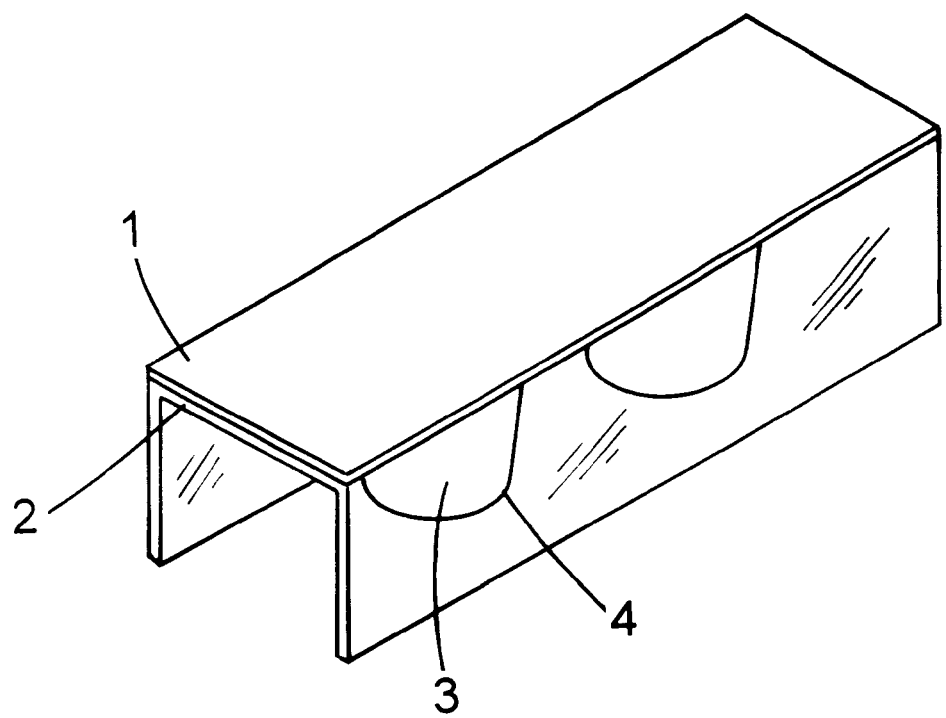
FIG. 1 is a perspective view of detecting kit according to this invention.

In the following detailed description, only the preferred embodiment of the invention has been shown and described, simply by way of illustration of the best mode contemplated by the inventors of carrying out the invention. As will be realized, the invention is capable of modification in various obvious respects, all without departing from the invention. Accordingly, the drawings and description are to be regarded as illustrative in nature, and not restrictive.

Hereinafter, further details of this invention are explained as follows:

In detecting H. pylori, the inventors tried to substantially lower false positive rates due to the subjectivity of the readers by transforming the existing urease enzyme tests from the methods conventionally used to a composition that uses a speedy change of colors that enables an accurate determination to be made rapidly by comparing the test results simultaneously with positive and negative controls. Namely, since test kits using existing urease enzyme tests detect the pH increase caused by $OH^-$ ions produced from the reaction of water with the ammonia generated by simply decomposing urea, the inventors tried to eliminate the ammonium ions themselves in order to increase the rate of pH change. To do this, the inventors applied the phenate method (Standard Methods for the Examination of Water and Wastewater 19th ed. 1995, American Public Health Association, pp 4–80~4–82.) used in quantification of ammonium ions.

The Urea decomposition process by urease is presented as following reaction formula:

[reaction formula 1]

$$(NH_2)_2CO + 2H_2O \rightarrow 2NH_3 + H_2CO_3 \text{ (irreversible reaction)}$$

(urea)

$$H_2CO_3 \leftrightarrow H^+ + HCO_3^- \text{ (reversible reaction)}$$

$$2NH_3 + 2H_2O \leftrightarrow 2NH_4^+ + 2OH^- \text{(reversible reaction)}$$

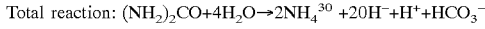

Total reaction: $(NH_2)_2CO + 4H_2O \rightarrow 2NH_4^{30} + 2OH^- + H^+ + HCO_3^-$ The constituents of this present invention increase pH promptly by transforming the products of the above described urea decomposition process, i.e., ammonium ions, into indophenol blue to continue urea decomposition. In order to achieve the above described purpose, the phenate method, a remarkably effective method of measuring ammonia concentration in the aqueous solution, is applied. The phenate method, using the principle that ammonia under a manganic catalyst reacts with hypochlorite base and phenol to change into indophenol blue, can be described as the following reaction formula:

[reaction formula 2]

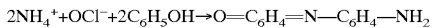

$$2NH_4^+ + OCl^- + 2C_6H_5OH \rightarrow O{=}C_6H_4{=}N{-}C_6H_4{-}NH_2$$

That is, the constituents of this invention make the reaction speed faster in order to increase pH rapidly by adding phenate reagent solution to constituents used in the conventional urease enzyme test and transforming ammonium ion generated in the urea decomposition process by the above described urease into indophenol blue.

Additionally, NaOCl is among the constituents that acts to reduce false positives that follow increased concentrations due to urease from bacilli as it has an inhibiting effect on weak urease activity. This also allows test results to be obtained after longer testing time periods.

In this invention, the added quantity of phenate reagent solution is adjusted within a range so that H. pylori urease activity is not inhibited and color change of the pH indicator is not affected. This invention's constituents and the possible content range of each components is as below:

urea from 0.5 to 4 vol %, $KH_2PO_4$ from 0.05 to 0.2 vol %, phenate reagent solution from 0.8 to 1.7 vol %, 0.002~0.005 vol % of an indicator having $pK_a$ from 6.5 to 8.5 and a balance of water From the above described composition, urea acts as a urease substrate which H. pylori produces, about 0.5~4 vol % of content is an appropriate level to measure activity of urease which H. pylori produces. $KH_2PO_4$ acting as a buffer solution should include 0.05~0.2 vol %, i.e., it can not obtain desired the pH range at lower than 0.05 vol % and tends to inhibit pH change at higher than 0.2 vol %. The phenate reagent solution, acting to transform ammonium ions into indophenol blue and to inhibit urease activities of other microorganisms should be included at 0.8~1.7 vol %, i.e, at lower than 0.8 vol % the effect of increasing the pH change speed by eliminating ammonium ions and the inhibiting effect of urease activity of other microorganisms are insufficient, while at higher than 1.7 vol % pH is increased much too high and the urease activities of other microorganisms as well as H. pylori tend to be inhibited. An indicator having a pKa from 6.5~8.5 acts to sense pH change, with phenol red being the most appropriate in this invention, preferably between 0.002~0.005 vol % for the precise determination. Phenol red has characteristics of showing yellow in an acid solution and a purplish-red color in a basic solution.

The above described phenate reagent solution containing in detail a manganous sulfate solution acting as a catalyst, hypochlorite reagent acting as a reactant reacted with ammonium ions and phenate reagent, and is especially desirably composed of 1 vol % manganous sulfate solution, 0.5 vol % hypochlorite reagent and 0.2 vol % phenate reagent. Moreover, it is further desirable that this constituent contains 0.5~2 vol % of a gelling agent, e.g., agar, as it can then be used conveniently in the form of a soft gel. It is preferable that constituent is controlled in the range of pH 6.0~7.8 because it aides precise determination when the pH is kept in this range.

Further desirable components and contents range of this invention's constituents are as follows:

2 vol % urea, 0.05 vol % $KH_2PO_4$, 1 vol % manganous sulfate solution, 0.5 vol % hypochlorite reagent, 0.2 vol % phenate reagent, 0.0025 vol % phenol red, 1 vol % agar, and a balance of water.

On the other hand, desirable components and contents of stock solution of phenate reagent solution used in this invention are as follows:

Manganous sulfate solution; 0.05 vol % $MnSO_4\ H_2O$, and a balance of distilled water, Hypochlorite reagent; 1 vol % NaOCl, and a balance of distilled water, Phenate reagent; 2.5 vol % NaOH, 8 vol % phenol, and a balance of distilled water.

This invention is to react with the above described constituents by placing biopsy tissue obtained through an endoscope on the gell made of the above described constituents and observe color change. The gell is made of he above described constituents and a positive control gell is produced by adding to the above described constituents a minimum quantity of NaOH that can show positive results, i.e., 10~20 $\mu l$ 0.1 N NaOH solution. A determination can be made as to whether or not there is an H. pylori infection comparing the color of the negative control gell in which NaOH is not added at all. Accordingly, a test device with positive and negative controls placed side by side for comparison at a glance with colors indicating positive or negative results will decrease erroneous test results due to the subjectivity of the reader.

Figure 2:
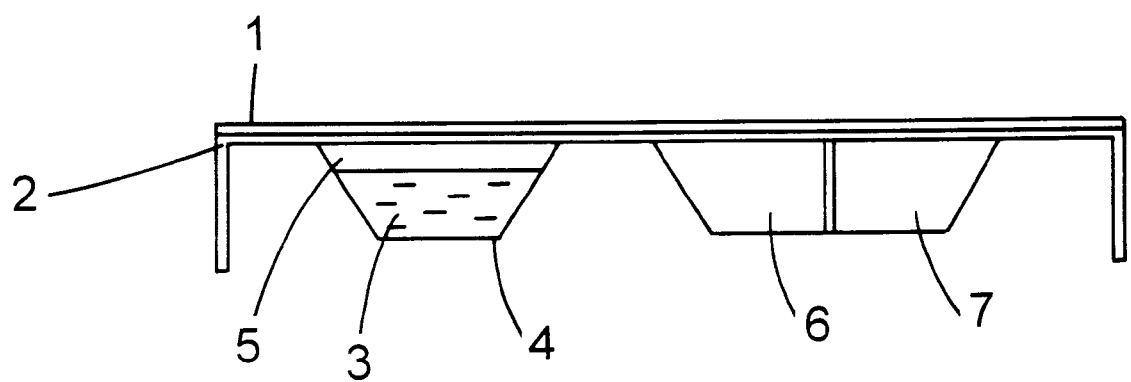
FIG. 2 is a sectional view of detecting kit according to this invention.
Figure 3:
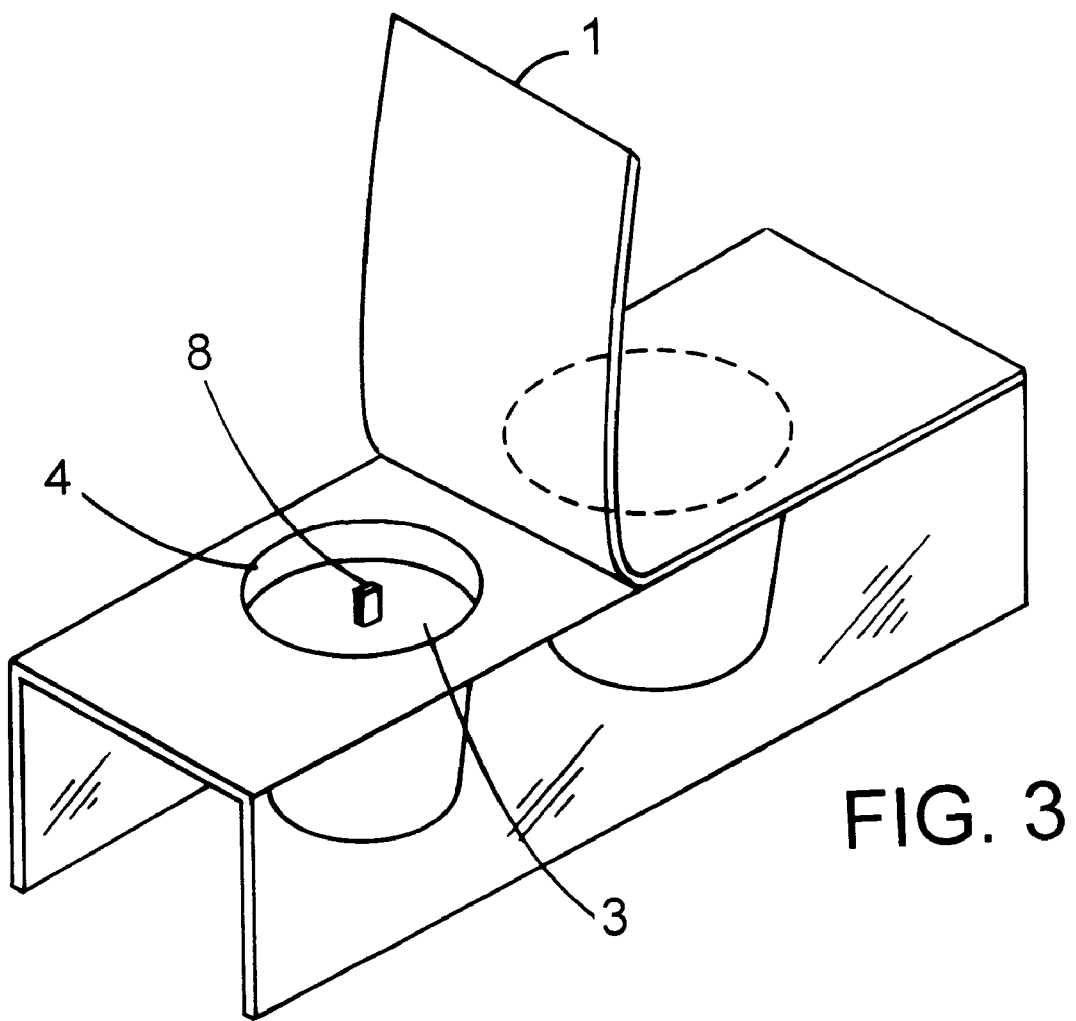
FIG. 3 is a drawing describing application example of detecting kit according to this invention.

A perspective view of a detecting kit according to this invention is presented in FIG. 1 and side view in FIG. 2, respectively. An application example of a detecting kit according to this invention is also presented in FIG. 3. Referring to the above described FIGS. 1 to 3, 1 is a cover, 2 is a container, most desirably a transparent container made of an acrylic material, 3 is detecting composition according to this invention, 4 is a test device, 5 is the biopsy specimen area, desirably opaquely treated such that biopsy specimen is not seen from the side, 6 is the negative control, 7 is the positive control and 8 is the biopsy sample.

A desirable practical example and comparative example of this invention are described. However, the below described practical example is only one of practical examples of this invention and this invention is not limited to the below described practical example.

[Practical Example 1]

Making H. pylori detecting compositions

First the below described composition of stock solution was prepared;

20 vol % urea, 2 vol % $KH_2PO_4$, 0.01 vol % phenol red, and 2 vol % agar.

As stock solution of phenate reagent, 100 ml of manganous sulfate solution was made by adding distilled water to $MnSO_4\ H2O$ 50 mg, 100 ml of hypochlorite reagent was made by adding distilled water to 10 ml of 10% NaOCl and the pH was adjusted to 6.8 with concentrated hypochloric acid. 100 ml of phenate reagent was prepared by adding distilled water to 2.5 g of NaOH and 8 ml of phenol. After the above described agar solution was autoclaved (121° C., 1.5 atm) for 15 minutes, it was left alone until it is used in the water tank at 55° C. and the below described 2 X reagent were produced.

A 50 ml mixture was made by mixing the above described 10 ml urea stock solution, 2.5 ml $KH_2PO_4$ stock solution, 25 ml phenol red stock solution, 1 ml manganous sulfate solution, 0.5 ml hypochlorite reagent and 0.2 ml phenate reagent and adding distilled water. After bacilli of the above described produced 2 X reagent were filtered out by 0.2 $\mu m$ filters, the same amount as 2% agar solution was mixed. As a result of that, the final concentration of the constituents was as below and the final pH was 7.5 at this time:

2% urea, 0.05% $KH_2PO_4$, 0.0005% manganous sulfate, 0.005% NaOCl, 0.2% phenate reagent (0.005% NaOH, 0.016% phenol), 0.0025% phenol red and 1% agar.

[Practical Example 2]

Manufacture of a H. pylori detecting kit

The composition manufactured from example 1 was injected into one wall of a multiwall plate, test device with biopsy tissue obtained from an endoscope, a positive control was made by injecting into another wall the composition manufactured and by further adding 10 $\mu l$ of 0.1 N NaOH to the above described composition, a negative control was made by injecting the above described composition into another wall, thereby making an H. pylori detecting kit. The above described detecting kit is called "PET (Pylori Easy Test) kit".

[Test Example 1]

After a patient's biopsy tissue was obtained, a CLOtest and PET of example 2 were used on that biopsy tissue simultaneouly, and the positive rate per hour was compared and the results were described in the below Table 1.

TABLE 1

| | Positive rate per hour | |
|---|---|---|
| Hour | PET | CLOtest |
| 1 | 10 | 3 |
| 2 | 10 (+0) | 3 (+0) |
| 3 | 13 (+3) | 8 (+5) |
| 4 | 13 (+0) | 8 (+0) |
| 12 | No test | No test |
| 24 | 13 (+0) | 10 (+2) |
| Total positive rate | 13/26 | 10/26 or 17/26* |

*7 readings were difficult to determine.

As a result, PET could confirm 76.9% of total positives within one hour and 100% after 3 hours. On the other hand, CLOtest could confirm only 17.6~30% of the positives and 100% only after 24 hours. However, uncertain color which could not be distinguished distinctly appeared after 24 hours and the positive rate was varied from 38.4% (10/26) to 65.3% (17/26) depending on the observers. Therefore, we can see that rapid dtermination is possible in the case where PET is used according to this invention.

After that, we observed the degree of consistency of PET results with the PCR method. Here, the PCR method used an amplifying method of 26 kDa protein gene, a method known as the most unique and sensitive in H. pylori detection (Ho, S, et al. 1991, Direct Polymerase Chain Reaction Test for detection of H. pylori in Human and Animals, J. Clin. Microbiol, 29 pp 2543~2549). The results were described the following table 2:

TABLE 2

| Consistency ratio with PCR method | |
|---|---|
| PET | CLOtest |
| 26/26 (100%) | 16/26 (61.5%): two false negatives, five false positives |
| | 21/26 (80.7%): when unreadable colors were judged to be negatives |

From the above described table 2, we can see that all of the 26 biopsy tissues are consistent with the results of the PCR method when using this PET invention and that the consistency ratio ranges between 61.5~80.7% for the Clotest. Therefore, we can see that it is possible to judge that this PET invention is more precise than Clotest.

[Test Example 2]

Biopsy tissue obtained during an endoscoping was refrigerated at −20° C. for 1 week, and the PET and CLOtest were then performed according to the same method as in test example 1 with the results compared and presented in table 3 and table 4.

TABLE 3

| | Positive rate per hour | |
|---|---|---|
| Hour | Practical example 1 | CLOtest |
| 1 | 6 | 1 |
| 2 | 11 (+5) | 2 (+1) |
| 3 | 13 (+2) | 4 (+2) |
| 4 | 13 (+0) | 8 (+4) |
| 12 | 13 (+0) | 12 (+0) |
| 24 | 13 (+0) | 12 (+0) |
| Total positive rate | 13/22 | 12/22* |

*6 readings were difficult to determine.

TABLE 4

| Consistency with PCR | |
|---|---|
| PET | CLOtest |
| 22/22 (100%) | 21/22 (95.5%); one false negative |
| | 18/22 (81.8%); when unreadable colors were judged to be negatives |

From table 3 and table 4, if PET according to this invention is used, it is notable that precise judgement is possible on biopsy tissue in which urease activity of H. pylori was decreased to certain degree.
promptly and precisely whether or not an H. pylori infection (the source bacterium causing gastrointestinal disorders) exists, and the same results can be obtained even after time has elapsed and the compositions are easily used in an endoscope chamber. The invention provides an H. pylori detecting kit and a method of using H. pylori detecting compositions.

[Test Example 3]

Urease decomposition capacity was examined on H. pylori bacterium and Staphlococcus hominis bacterium separated from biopsy tissue obtained during an endoscoping in order to examine the H. pylori peculiarity of PET.

The examination method involved first having H. pylori bacterium and S. hominis bacterium cultivated and diluted in sterilized distilled water so as to have an appropriate number of bacilli, and then PET and CLOtest were performed and compared according to the same method as in test example 1. The results were described in table 5.

TABLE 5

| Peculiarity comparison on H. pylori bacterium and S. hominis bacterium | | | |
|---|---|---|---|
| Classification | | UBPH (0.02%) | CLOtest |
| H. pylori | $10^5$ cells | <30 min | within 30 min |
| | $10^4$ cells | 1 h | 2 h |
| | $10^3$ cells | No response even after 24 hours | No response even after 24 hours |
| S. hominis | $10^7$ cells | 8 h | 6 h |
| | $10^6$ cells | No response even after 24 hours | 10 h |

From the above described table 5 it is noted that if PET according to this invention is used, high peculiarity detection is possible with urease activity of H. pylori showing a fast response and urease activity of other bacilli showing low response.

Although preferred embodiments of the present invention have been described in detail hereinabove, it should be clearly understood that many variations and/or modifications of the basic inventive concepts herein taught which may appear to those skilled in the pesent art will still fall within the spirit and scope of the present invention, as defined in the following claims.

What is claimed is:

1. A composition for detecting *Helicobacter pylori* including:
   a) urea from 0.5 to 4 vol %;
   b) $KH_2PO_4$ from 0.05 to 0.2 vol %;
   c) phenate reagent solution from 0.8 to 1.7 vol %;
   d) an indicator having a $pK_a$ of 6.5 to 8.5, 0.002 to 0.005 vol %; and
   e) a balance of water.

2. The composition of claim 1 wherein said phenate reagent solution from 0.8 to 1.7 vol % of said *Helicobacter pylori* detecting composition comprises:
   a) manganous sulfate solution from 0.5 to 1 vol %;
   b) hypochlorite reagent from 0.2 to 0.5 vol %; and
   c) phenate reagent from 0.1 to 0.2 vol %.

3. The composition of claim 1 wherein said composition is a *Helicobacter pylori* detecting composition in which the indicator is phenol red.

4. The composition of claim 1 wherein said composition is a *Helicobacter pylori* detecting composition further including gelling agent from 0.5 to 2 vol %.

5. The composition of claim 4 wherein said composition is a *Helicobacter pylori* detecting composition including:
   a) 2 vol % urea;
   b) 0.05 vol % $KH_2PO_4$;
   c) 1 vol % manganous sulfate solution;
   d) 0.5 vol % hypochlorite reagent;
   e) 0.2 vol % phenate reagent;
   f) 0.0025 vol % phenol red;
   g) 1 vol % agar; and
   h) a balance of water.

6. The composition of claim 1 wherein said composition is a *Helicobacter pylori* detecting composition having a pH from 6.0 to 7.8.

7. A kit for detecting *Helicobacter pylori* including:
   a) test device made of composition according to claim 4, wherein biopsy tissue is placed;
   b) positive control manufactured by further adding 10~20 µl of 0.1 N NaOH solution to composition of claim 4; and
   c) negative control manufactured from composition of claim 4, where biopsy tissue is not placed.

8. A method of detecting *Helicobacter pylori* from biopsy tissue comprising the steps of:
   a) reacting biopsy tissue and said composition according to claim 1; and
   b) observing the color change of the said biopsy tissue reacted composition.

* * * * *